United States Patent [19]

Verheyden et al.

[11] Patent Number: 4,704,392

[45] Date of Patent: Nov. 3, 1987

[54] TRICYCLIC DERIVATIVES OF SUBSTITUTED PYRIMIDINES

[75] Inventors: Julien P. H. Verheyden, Los Altos, Calif.; John C. Martin, Fayetteville, N.Y.; G. V. Bindu Madhavan, Palo Alto, Calif.; Daniel P. C. McGee, Mountain View, Calif.; Ernest J. Prisbe, Los Altos, Calif.

[73] Assignee: Syntex (U.S.A.) Inc., Palo Alto, Calif.

[21] Appl. No.: 851,591

[22] Filed: Apr. 14, 1986

Related U.S. Application Data

[62] Division of Ser. No. 728,954, Apr. 30, 1985, Pat. No. 4,605,659.

[51] Int. Cl.[4] ................. A61K 31/42; C07D 239/80
[52] U.S. Cl. ........................................ 514/267; 544/250
[58] Field of Search ................... 536/23; 544/250; 514/267

[56] References Cited

U.S. PATENT DOCUMENTS 3,709,874  1/1973  Moffatt et al. ................. 536/23
4,177,348  12/1979  Shealy et al. ................. 544/250

FOREIGN PATENT DOCUMENTS 2601399  1/1976  Fed. Rep. of Germany .

OTHER PUBLICATIONS

*Journal of Heterocyclic Chemistry*, vol. 13, pp. 1015-1020.

Primary Examiner—Donald G. Daus
Assistant Examiner—B. Cassatt
Attorney, Agent, or Firm—Annette Moore; Tom Moran

[57] ABSTRACT

Compounds useful as antiviral agents are depicted in the formula:

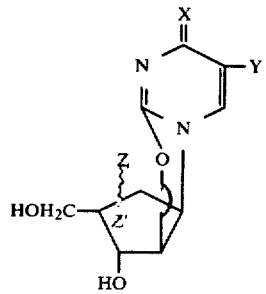

wherein: X is oxygen or NH, Y is hydrogen, iodo, fluoro, methyl or trifluoromethyl, Z is hydrogen or fluoro and Z' is fluoro; and the wavy line indicates that the group may be above or below the plane of the ring; and the pharmaceutically acceptable acid addition salts thereof.

3 Claims, No Drawings

TRICYCLIC DERIVATIVES OF SUBSTITUTED PYRIMIDINES

This is a division of application U.S. Ser. No. 728,954 filed Apr. 30, 1985, now U.S. Pat. No. 4,605,659.

BACKGROUND OF THE INVENTION

1. Field of the Invention

This invention relates to 4-substituted-5-(hydroxymethyl)-1, 2-cyclopentanediols and 1-cyclopentanols substituted at the 3-position by various heterocyclic groups and the pharmaceutically acceptable acid addition salts thereof which are useful as antiviral agents. The invention also relates to pharmaceutically acceptable composition containing an effective amount of at least one of the compounds. The invention also relates to a process for making the compounds of the invention.

2. Related Disclosure

Aristeromycin and certain aristeromycin derivatives are known. See, for example, Japanese Pat. No. 7023596, Japanese Patent Application No. 57094288, U.S. Pat. No. 4,177,348, U.S. Pat. No. 4,138,562, U.S. Pat. No. 4,232,154, U.S. Pat. No. 4,396,623 and European Patent 104,066. A novel class of 5-hydroxymethyl-1,2-cyclopentanediols and 1-cyclopentanols wherein the 4-position of the cyclopentane ring is substituted has now been prepared.

SUMMARY OF THE INVENTION

The first aspect of the invention is the group of compounds represented by the formula:

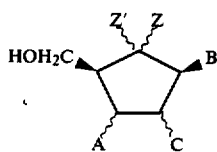
(I)

wherein
A is hydroxy; and
C is hydrogen or hydroxy;
B is a heterocyclic ring selected from the group consisting of 2-amino-6-hydroxypurin-9-yl, 6-aminopurin-9-yl, 2,4-dioxopyrimidin-1-yl optionally substituted at the 5-position by fluoro, methyl, iodo, trifluoromethyl, 2-bromovinyl. 2-chlorovinyl or 2-iodovinyl, and 4-amino-2-oxopyrimidin-1-yl optionally substituted at position-5 by iodo or trifluoromethyl;
Z is hydrogen and Z' is hydroxy or fluoro; or
Z and Z' are both fluoro; or
Z together with Z' is oxo; and
the wavy line indicates that the group may be above or below the plane of the ring; and
the pharmaceutically acceptable acid addition salts thereof.

The second aspect of the invention is a composition useful for treating RNA and DNA viral infections which composition comprises an effective amount of at least one compound of formula (I) or compound of formula (XIII) or a pharmaceutically acceptable acid addition salt thereof and a pharmaceutically acceptable excipient.

Another aspect of the invention is a method for treating warm-blooded and cold-blooded animals for RNA and DNA viral infections which comprises administering an effective amount of at least one compound of formula (I) or compound of formula (XIII).

Another aspect of the invention is a process for preparing the compounds of the formula:

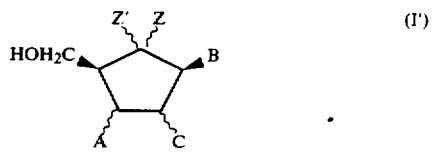
(I')

wherein
A is hydroxy; and
C is hydrogen or hydroxy;
B is a heterocyclic ring selected from the group consisting of 2-amino-6-hydroxypurin-9-yl, 6-aminopurin-9-yl, 2,4-dioxopyrimidin-1-yl optionally substituted at the 5-position by fluoro, methyl, iodo, trifluoromethyl, 2-bromovinyl. 2-chlorovinyl or 2-iodovinyl, and 4-amino-2-oxopyrimidin-1-yl optionally substituted at position-5 by iodo or trifluoromethyl;
Z and Z' are independently hydrogen, fluoro, hydroxy or Z together with Z' is oxo;
the wavy line indicates that the group may be above or below the plane of the ring; and
the pharmaceutically acceptable acid addition salts thereof.

Another aspect of the invention is the compound of the formula

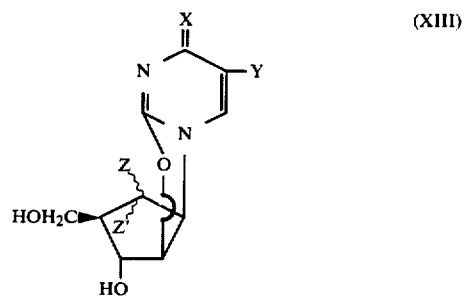
(XIII)

wherein
X is oxygen or NH, Y is hydrogen, iodo, fluoro, methyl or trifluoromethyl;
Z is hydrogen or fluoro and Z' is fluoro; and the wavy line indicates that the group may be above or below the plane of the ring; and the pharmaceutically acceptable acid addition salts thereof.

DETAILED DESCRIPTION AND PREFERRED EMBODIMENT

The broadest aspect of the present invention is the group of compounds represented by the formula:

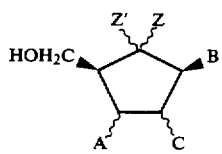
(I)

wherein
A is hydroxy; and
C is hydrogen or hydroxy;

B is a heterocyclic ring selected from the group consisting of 2-amino-6-hydroxypurin-9-yl; 6-aminopurin-9-yl, 2,4-dioxopyrimidin-l-yl optionally substituted at the 5-position by fluoro, methyl, iodo, trifluoromethyl, 2-bromovinyl, 2-chlorovinyl or 2-iodovinyl, and 4-amino-2-oxopyrimidin-l-yl optionally substituted at position-5 by iodo or trifluoromethyl;

Z and Z' are independently hydrogen, fluoro, hydroxy or Z together with Z' is oxo;

the wavy line indicates that the group may be above or below the plane of the ring; and the pharmaceutically acceptable acid addition salts thereof.

Another aspect of the present invention are the compounds of the formula

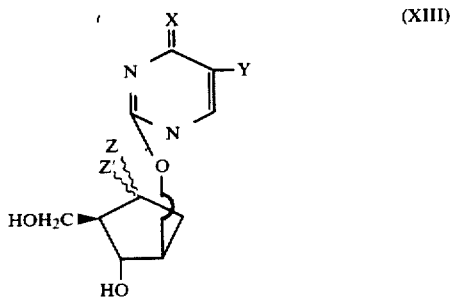

(XIII)

wherein

X is oxygen or NH, Y is hydrogen, iodo, fluoro, methyl or trifluoromethyl;

Z is hydrogen or fluoro and Z' is fluoro; and the wavy line indicates that the group may be above or below the plane of the ring; and the pharmaceutically acceptable acid addition salts thereof.

A preferred group of compounds of formula (I) is that wherein B is 2,4-dioxo-5-fluoropyrimidinyl or 2,4-dioxopyrimidinyl and A and C are both hydroxy. Within this group it is preferred that at least one Z or Z' is fluoro.

Another preferred group of compounds of formula (I) is that wherein A is hydroxy and C is hydrogen and B is 2,4-dioxoprymidinyl substituted in the 5-position by iodo, fluoro, trifluoromethyl, 2-bromovinyl or 2-iodovinyl.

As used in the specification and appended claims, unless specified to the contrary, the following terms have the meaning indicated. "Heterocyclic ring precursor" is a group which can be cyclized to the group "B" of the instant compounds. "Alkoxy" refers to the group R'O— wherein R' is an alkyl group of one to four carbon atoms.

In naming the compounds of the instant invention the following numbering systems for the rings will be used:

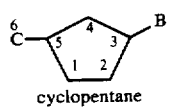

cyclopentane

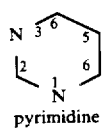

pyrimidine

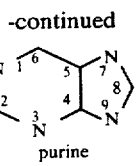

purine

It is understood that a group above the plane of the ring is signified by "β" and the group below the plane of the ring is signified by "α".

It is further understood that the definition of X as hydroxy or amino on the pyrimidine ring also encompasses the tautomeric oxo form or imino form.

Compounds of formula (I) may exist as stereoisomers.

Certain compounds of the present invention possess asymmetric carbons and may be prepared in either optically active form, or as a racemic mixture. Unless otherwise specified, such compounds described herein are all in the racemic form. However, the scope of the subject invention herein is not to be considered limited to the racemic form but to encompass the individual optical isomers of the subject compounds.

If desired, racemic products prepared herein may be resolved into their optical antipodes by conventional resolution means known per se, for example, by the separation (e.g., fractional crystallization) of the diastereomeric esters formed by reaction of, e.g. racemic compounds of formula (I) with an optically active acid or acid chloride. Exemplary of such optically active acids and acid chlorides are the optically active forms of camphor-10-sulfonic acid, α-bromocamphor-π-sulfonic acid, camphoric acid, menthoxyacetic acid, tartaric acid, malic acid, diacetyltartaric acid, 6-methyoxynaphth-2-y 1-2-propanoyl chloride, pyrrolidone-5-carboxylic acid, dibenzoyltartaric acid, and the like. The separated pure diastereomeric esters may then be cleaved by standard means to afford the respective optical isomers of the compounds of formula (I).

Another method of preparing the optical isomers of compounds of formula (I) is by separating the racemic intermediate of formula (VIII) into the individual isomers by the methods described above and then proceeding with the individual isomers to prepare the optically active compounds of formula (I)

UTILITY AND ADMINISTRATION

The subject compounds of formula (I) and formula (XIII) exhibit potent antiviral activity against both RNA and DNA viruses when administered to warm blooded and cold blooded animals, particularly mammals, birds, and fish, but most particularly humans. For example, the compounds of the present invention exhibit excellent activity against Herpes Simplex virus I and II and related viruses such as cytomegalovirus, Epstein-Barr virus and varicella Zoster virus as well as viral hepatitis such as hepatitis B.

The compounds of the instant invention are also active against influenza, parainfluenza, rhino and respiratory syncytial viruses.

Pharmaceutical compositions, both veterinary and human, containing the subject compound appropriate for antiviral use are prepared by methods and contain excipients which are well known in the art. A generally recognized compendium of such methods and ingredients is Remington's Pharmaceutical Sciences by E. W. Martin, (Mark Publ. Co., 15th Ed., 1975). Liposomes may also be employed as pharmaceutical compositions for the compounds of formula (I), using methods known to those in the art [for example, as described in Szoka, F. Jr. et al, *Ann.Rev.Biophys.Bioeng.* 9:467–508 (1980), Schullery, S. E. et al, *Biochemistry* 19: 3919–3923 (1980) and Gregoriadis, G. et al, "Liposomes in Biological Systems," John Wiley and Sons (1980)].

The compounds of the invention may be administered parenterally (for example, by intravenous, subcutaneous, intraperitoneal or intramuscular injection), orally, topically, intranasally or rectally.

The compositions are administered orally or parenterally at does levels of about 0.1 to 300 mg/kg of compound of formula (I) or compound of formula (XIII), preferably 1.0 to 30 mg/kg of mammal body weight, and are used in man in a unit dosage form, administered one to five times daily in the amount of 10 to 500 mg per unit dose. For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated. The amount of compound of formula (I) or compound of formula (XIII) in the formulation may vary from 0.1 percent weight (% w) to 99% w or more of the compound based on the total formulation and about 1% w to 99.9% w excipient. Preferably the compound is present at a level of 10%–95% w.

For parenteral administration or for administration as drops, as for eye infections, the compounds may be presented in aqueous solution in a concentration of from about 0.1 to 10%, more preferably about 0.1 to 7%. The solution may contain antioxidants, buffers, and other suitable additives.

Alternatively for infections of the eye, or other external tissues, e.g. mouth and skin, the compositions are preferably applied to the infected part of the body of the patient topically as an ointment, cream, aerosol or powder, preferably an an ointment or cream. The compounds may be presented in an ointment, for instance with a water soluble ointment base, or in a cream, for instance with an oil in water cream base, in a concentration of from about 0.01 to 10%; preferably 0.1 to 7%, most preferably about 4.0% w/v. Additionally, viral infections may be treated by use of a sustained release drug delivery system as is described in U.S. Pat. No. 4,217,898.

For aerosol administration, the active ingredient is preferably supplied in finely divided form along with a surfactant and a propellant. Typical percentages of active ingredients are 0.01 to 50% by weight, preferably 0.04 to 10.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

The compounds of the present invention or compositions containing same are also useful in treating non-human mammals, birds, e.g., chickens and turkeys, and cold-blooded animals, e.g., fish. For example, the compounds of the present invention and compositions containing same exhibit antiviral activity against the following non-human viruses:

Sciruid herpes virus 1
Cavlid herpes virus 1
Lagomorph herpes virus 1
Phasianid herpes virus 1
Phasianid herpes virus 2 (Marek's disease)
Turkey herpes virus 1
Anatid herpes virus 1
Catfish herpes virus 1
Equid herpes virus 3
Bovid herpes virus 1
Bovid herpes virus 2
Bovid herpes virus 3
Bovid herpes virus 4
Pig herpes virus 1
Pig herpes virus 2
Murid herpes virus 1
Cebid herpes virus 1
Cebid herpes virus 2
Tupaiid herpes virus 1
Canine herpes virus 1
Feline herpes virus 1
Equid herpes virus 1
Equid herpes virus 2

Avian viral diseases such as Marek's disease and the like are prevented and/or treated by compounds of the present invention by methods well-known in the veterinary art such as by injecting the birds with the composition containing the compound, or by adding the compound of the instant invention to feed or drinking water.

Fish which are in a confined area such as a pool, aquarium or holding tank may also be treated for viral infections such as herpes-like viruses, e.g., channel catfish virus (CCV), herpes-virus salomones, Nerka virus and the like by adding the compound directly to the water of the pool, aquarium or holding tank or by incorporating the compounds into the feed.

The compounds of the present invention are also useful for treating mammals suffering from upper and lower respiratory tract infections such as human and bovine RSC.

The exact regimen for administration of the compounds and compositions disclosed herein will necessarily be dependent upon the needs of the individual subject being treated, the type of treatment and, of course, the judgment of the attending practitioner.

PREPARATION

The novel process for preparing compounds of formula (I') which encompasses the compounds for formula (I) is shown below. Compounds of formula (XIII) may be prepared from compounds of formula (I).

REACTION SEQUENCE

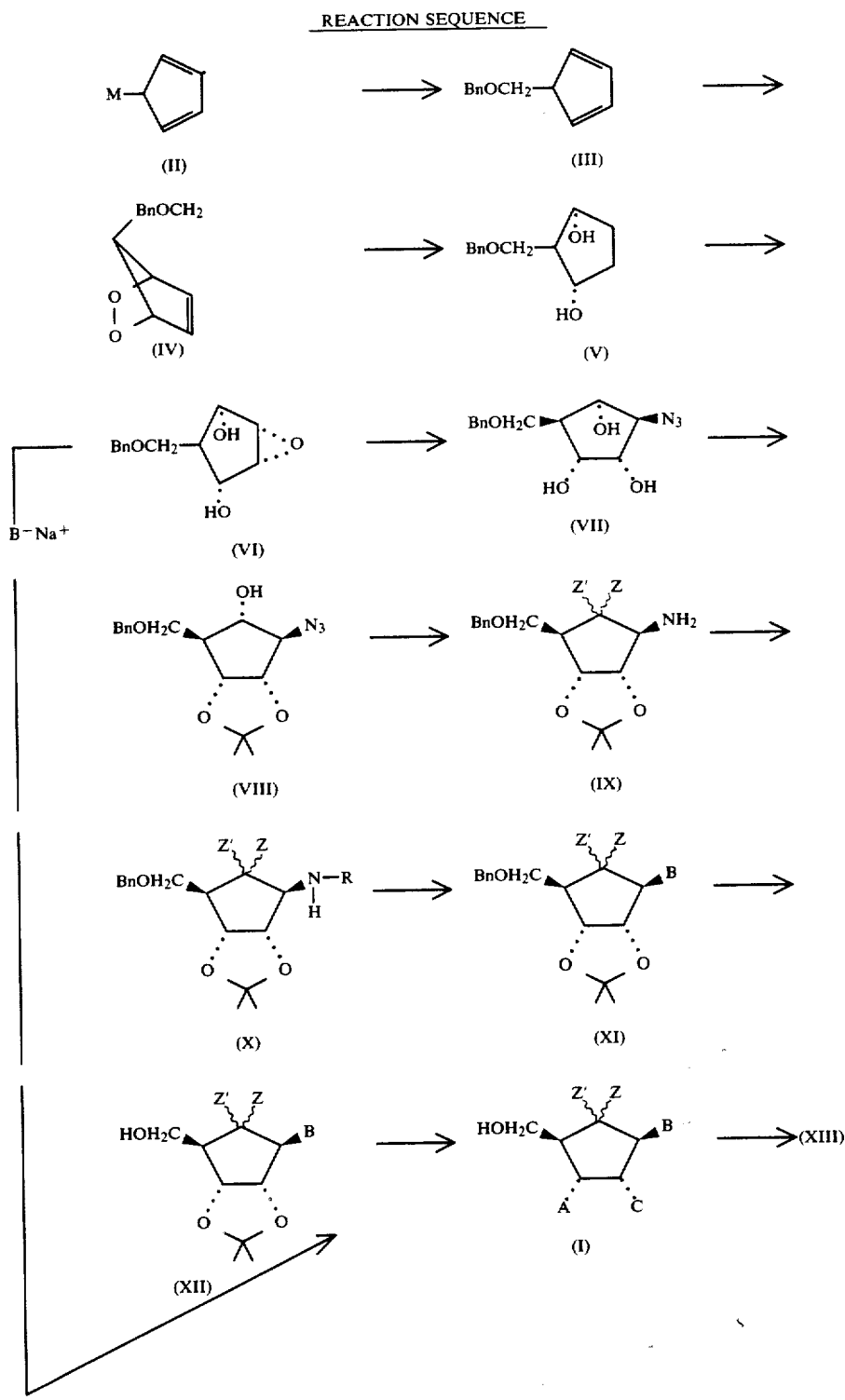

wherein Bn is benzyl, M is a metal, A, B, C, Z and Z' are as defined above and R is a heterocyclic ring precursor.

Compound of formula (II), available from Alpha Chemical Co., is reacted with benzyl chloromethyl ether to form a compound of formula (III). The chloromethyl ether is added dropwise to a metal derivative of cyclopentadiene, e.g., sodium, potassium or thallium, preferably thallium cyclopentadiene of formula (II) over 15 to 60 minutes, preferably over 15 to 45 minutes suspended in a solvent such as diethyl ether. The suspension is stirred at $-25°$ to $0°$ C. for 10 to 24 hours, preferably at $-25°$ to $-15°$ C. for 12 to 20 hours. The suspension is filtered and compound of formula (III) is recovered by evaporation of the filtrate. Without purification compound of formula (III) is dissolved in a solvent such as methanol cooled to $-20°$ C. and oxidized to the novel compound of formula (IV) which is reduced to compound of formula (V) is situ by adding compound of formula (III) in methanol to a solution of thiourea dissolved in a solvent such as methanol which is saturated with oxygen containing an oxygen sensitizer such as Rose Bengal. The solution is held at $-5°$ C. while it is irradiated for 5 to 12 hours, preferably for 7 to 10 hours with a mercury immersion lamp. Oxygen is continuously added throughout the irradiation. Compound of formula (V) is recovered by evaporation of the solvent and purified by, e.g., chromatography.

Compounds of formula (III) may also be oxidized to compound of formula (IV) with a peroxy compound such as hydrogen peroxide and sodium hypochlorite mixture.

Compound of formula (V) is converted to compound of formula (IV) by dissolving compound (V) in a solvent such as dichloromethane and treating compound (V) with an oxidizing agent such as a carboxylic peroxy acid such as perbenzoic acid, m-chloroperbenzoic acid, peracetic acid, and the like. The epoxide of formula (VI) is recovered by e.g. chromatography or solvent extraction.

Compound of formula (VII) is prepared by dissolving compound of formula (VI) in a solvent such as dimethylformamide, N-methyl-2-pyrrolidone and the like, adding an alkali metal azide, e.g., sodium azide and heating to 50° to 150°, preferably 80° to 120° C. for 6 to 24 hours, preferably for 8 to 16 hours. Compound of formula (VII) is recovered as an oil which is purified by e.g. chromatography.

The azide of formula (VII) is reacted with 2,2-dimethoxypropane in a solvent such as acetone and the like in the presence of a strong acid such as perchloric acid, hydrochloric acid and the like. The solution is stirred at room temperature to 50° C., preferably at room temperature for 15 minutes to 3 hours, preferably for ½ to 1 hour. After neutralizing with a base such as sodium hydroxide or ammonium hydroxide, the resulting oil is purified by, e.g., chromatography.

The azide of formula (VIII) is converted to the amine of formula (IX) by catalytic hydrogenation.

A suspension of compound of formula (VIII) in an alcohol such as methanol, ethanol, isopropanol and the like in the presence of the catalyst such as palladium on calcium carbonate is maintained under a positive hydrogen pressure for 6 to 24 hours, preferably for 8 to 16 hours. After removal of the catalyst compound of formula (IX) wherein Z is OH and Z' is hydrogen is recovered by, e.g., chromatography. Compound of formula (IX) wherein Z is fluoro and Z' is hydrogen is prepared by reacting the hydroxy group at position-4 with a sulfonic acid anhydride or sulfonic acid chloride such as trifluoromethanesulfonic anhydride, methanesulfonic anhydride, toluenesulfonic chloride and the like followed by reaction with a fluorinating agent such as tris (dimethylamino) sulfonium difluorotrimethylsilicate. Compound of formula (VIII) in a solvent such as dichloromethane and a sulfonic anhydride or chloride is stirred at room temperature for 15 minutes to 2 hours, preferably for 30 minutes to ½ hours. The solvent is removed and the sulfonate of compound of formula (VIII) is recovered.

The sulfonate in a solvent such as tetrahydrofuran and the like is fluorinated with, e.g., tri(dimethylamino) sulfonium difluorotrimethylsilicate available, i.a., from Aldrich Chemical Co. The solution is heated under reflux for 6 to 24 hours, preferably for 8 to 16 hours. The azide group is reduced to the amino group by the method described above. Compound of formula (IX) wherein Z is fluoro and Z' is hydrogen is recovered and purified by, e.g., chromatography. Where Z together with Z' is oxo compound of formula (IX) is prepared by oxidizing compound of formula (VIII) with, e.g., pyridinium chloro chromate. Where Z and Z' are both fluoro compound of formula (IX) is prepared by the method described in *J. Org. Chem.*, 40(5):574 (1975).

When both Z and Z' are hydrogen, compound of formula (IX) is prepared by first converting the 4-hydroxy group to a sulfonate group by the method described above. This compound is reacted with lithium iodide in a solvent such as dimethylformamide and the like at room temperature for ½ to 3 hours, preferably for ½ to 2 hours. The iodide compound is purified by, e.g., chromatography and the iodide group is removed by catalytic hydrogenation. The iodide compound in a solvent such as methanol is shaken in a Parr bomb in the presence of, e.g., palladium on carbon and hydrogen at room temperature for 2 to 12 hours, preferably for 3 to 8 hours. The azide group is also reduced to the amino group.

Compound of formula (IX) is reacted with a reagent which yields a group, R, to form compound of formula (X). Compound of formula (X) is cyclized to compound of formula (XI).

When the desired B is an optionally substituted purine ring, compound of formula (IX) is reacted with 5-amino-4,6-dichloropyrimidine to form compound of formula (X) wherein R is 5-amino-6-chloropyrimidin-4-yl. Compound of formula (IX) in a solvent such as N-methylpyrrolidone and the like in the presence of a base such as pyridine, triethylamine and the like are reacted with 5-amino-4,6-dichloropyrimidine at 100° to 220° C., preferably at 150° to 200° C. for 6 to 24 hours, preferably for 8 to 16 hours. Compound of formula (X) is recovered by extraction and chromatography.

Another method for preparing compounds of formula (XI) wherein Z and Z' are both hydrogen is by reacting compound of formula (XI) wherein Z is hydroxy and Z' is hydrogen with 1,1-diimidazolylthiocarbonyl to form the intermediate of formula (XI) wherein the 4-position is substituted by 1-imidazolylthiocarbonyloxy group. The 1-imidazolylthiocarbonyloxy group is removed by reduction with tributyl tin hydride.

Compound of formula (XI) wherein B is an optionally substituted purine is prepared from compound of formula (X) wherein R is 5-amino-6-chloropyrimidin-4-yl by reacting with diethoxymethylacetate or trialkyl orthoformate, preferably trimethyl or triethyl orthoformate. A mixture containing diethoxymethylacetate and the above compound of formula (X) is heated at 75° to 150° C., preferably from 75° to 125° C. for 30 minutes to 2 hours, preferably from 30 minutes to 1½ hours. Compound of formula (XI) wherein B is 6-chloropurin-9-yl is recovered by, e.g., chromatography. When the orthoformate is used, compound of formula (X) and the orthoformate are dissolved in dry toluene containing hydrogen chloride.

When the desired B is an optionally substituted pyrimidine as defined above, compound of formula (X) wherein R is an (alkoxyethenylcarbonyl) aminocarbonyl is prepared by reacting compound of formula (IX) with an alkoxyacryloylisocyanate such as ethoxyacrylolyisocyanate to form the above urea of formula (X). The alkoxyacryloylisocyanate is prepared by the method described in *J. Heterocyclic Chem.*, 13:1015 (1976). An alkoxyacrylic acid is converted to its sodium salt by reaction with sodium hydroxide which is then reacted with thionyl chloride. The chloride is converted to the isocyanate by reaction with a metal cyanate such as silver cyanate. The chloride in a solvent such as benzene is added to a refluxing solution of benzene and the metal cyanate. After the addition is complete the mixture is heated for 15 minutes to one hour, preferably for 30 minutes, followed by stirring for 1 to 4 hours, preferably for 2 to 3 hours at room temperature. The resultant solution containing the isocyanate was added dropwise to dry dimethylformamide solution of compound of formula (IX) under dry nitrogen at −20° to 0° C., preferably at −15° C. to −5° C. After addition the mixture is allowed to warm to room temperature and stirred at room temperature overnight. Compound of formula (X) is recovered by recrystallization from, e.g., ether when R is N'-(2-ethoxy-1-methylethenylcarbonyl) aminocarbonyl, alkoxymethacryloylisocyanate is used in the above process.

The following compounds of formula (X) wherein R is N'-(2-ethoxyethenylcarbonyl) aminocarbonyl or N'-(2-ethoxy-1-methylethenylcarbonyl) aminocarbonyl, Z is hydroxy, fluoro or hydrogen and Z' is fluoro or hydrogen may be prepared by the above methods:

3-(N'-(2-ethoxyethenecarbonyl)aminocarbonylamino)-4-fluoro-5-benzyloxymethyl-1, 2-isopropylidenedioxycyclopentane;

3-(N'-(2-ethoxyethenecarbonyl)aminocarbonylamino)-4,4-difluro-5-benzyloxymethyl-1,2-isopropylidenedioxycyclopentane;

3-(N'-(2-ethoxyethenecarbonyl)aminocarbonylamino)-4-hydroxy-5-benzyloxymethyl-1, 2-isopropylidenedioxycyclopentane;

3-(N'-(2-ethoxyethenecarbonyl)aminocarbonylamino)-4-oxo-5-benzyloxymethyl-1, 2-isopropylidenedioxycyclopentane;

3-(N'-(2-ethoxy-1-methylethenecarbonyl)aminocarbonylamino)-4-fluoro-5-benzyloxymethyl-1, 2-isopropylidenedioxycyclopentane;

3-(N'-(2-ethoxy-1-methylethenecarbonyl)aminocarbonylamino)-4,4-difluoro-5-benzyloxymethyl-1, 2-isopropylidenedioxycyclopentane;

3-(N'-(2-ethoxy-1-methylethenecarbonyl)aminocarbonylamino)-4-hydroxy-5-benzyloxymethyl-1, 2-isopropylidenedioxycyclopentane; and 3-(N'-(2-ethoxy-1-methylethenecarbonyl)aminocarbonylamino)-4-oxo-5-benzyloxymethyl-1, 2-isopropylidenedioxycyclopentane.

Compound (X) is cyclized in the presence of an acid catalyst such as sulfuric acid, toluenesulfonic acid and the like. Compound (X) and the acid catalyst are heated under reflux for 1 to 5 hours, preferably for 2½ to 4 hours. After cooling, the solution is diluted with water and neutralized with a base such as sodium hydroxide. Compound of formula (XI) wherein B is pyrimidinyl is recovered by recrystallization from e.g. cyclohexane.

The following compounds of formula (XI) wherein B is an optionally substituted pyrimidinyl group as defined above are prepared by the above methods:

3-(2,4-dioxo-5-methylpyrimidin-1-yl)-4-fluoro-5-benzyloxymethyl-1, 2-isopropylidenedioxycyclopentane;

3-(2,4-dioxo-5-methylpyrimidin-1-yl)-4,4-difluoro-5-benzyloxymethyl-1, 2-isopropylidenedioxycyclopentane;

3-(2,4-dioxo-5-methylpyrimidin-1-yl)-4-hydroxy-5-benzyloxymethyl-1, 2-isopropylidenedioxycyclopentane;

3-(2,4-dioxo-5-methylpyrimidin-1-yl)-4-oxo-5-benzyloxymethyl-1, 2-isopropylidenedioxycyclopentane;

3-(2,4-dioxopyrimidin-1-yl)-4-fluoro-5-benzyloxymethyl-1,2-isopropylidenedioxycyclopentane;

3-(2,4-dioxopyrimidin-1-yl)-4,4-difluoro-5-benzyloxymethyl-1,2-isopropylidenedioxycyclopentane;

3-(2,4-dioxopyrimidin-1-yl)-4-hydroxy-5-benzyloxymethyl-1,2-isopropylidenedioxycyclopentane; and 3-(2,4-dioxopyrimidin-1-yl)-4-oxo-5-benzyloxymethyl-1,2-isopropylidenedioxycyclopentane.

The benzyl group on compound of formula (XI) wherein B is 6-aminopurinyl is removed by transfer hydrogenolysis. An ethanol suspension of compound of formula (XI) with a catatyst such as palladium hydroxide on carbon containing cyclohexene, 1,4-cyclohexadiene and the like is refluxed for 3 to 12 hours, preferably for 4 to 8 hours. After removal of the catalyst by filtration compound of formula (XII) is recovered and purified by, e.g., chromatography.

Compounds of formula (I) wherein A and C are hydroxy are prepared from compound of formula (XII) by removal of the isopropylidene group by acidic hydrolysis using, e.g., acetic acid, hydrochloric acid and the like. Compound of formula (XII) in the acid is heated at 50° C. to 100° C., preferably at 55° to 75° C. for 15 minutes to 1½ hours, preferably for 15 minutes to 45 minutes. After concentration of the solution, compound of formula (I) is recovered by recrystallization from, e.g., ethyl acetate-methanol.

When B is 2,4-dioxo-5-fluoropyrimidin-1-yl compound of formula (I) may be prepared by fluorinating the 2,4-dioxopyrimidin-1-yl ring with trifluoromethyl hypofluorite or elemental fluorine according to the method described in *J. Med. Chem.*, 24(9):1083 (1981). To compound of formula (I) wherein B is 2,4-dioxopyrimidin-1-yl in acetic acid is bubbled a fluorine-nitrogen mixture for 5 minutes to 30 minutes, preferably for 10 minutes. The solution is then concentrated to dryness and the compound of formula (I) wherein B is 2,4-dioxo-5-fluoropyrimidin-1-yl is recovered by extraction with ethanol.

Compound of formula (I) wherein B is 4-amino-2-oxopyrimidin-1-yl may be prepared by the method described in *J. Heterocyclic Chem.*, 17:353 (1980). Compound of formula (I) wherein B is 2,4-dioxopyrimidin-1-yl in a solvent such as dimethylformamide is reacted with thionyl chloride which replaces one oxo group on the ring by a chloro group. The mixture is heated under reflux for 4 to 10 hours, preferably for 3 to 8 hours. The chloro compound is recovered by concentration under reduced pressure. The resultant solid dissolved in a solution of ammonia in methanol is heated in a Parr bomb at 80° to 150° C., preferably at 90° to 110° C. for 12 to 36 hours, preferably for 16 to 24 hours. Compound of formula (I) wherein B is 4-amino-2-oxopyrimidin-1-yl is recovered by recrystallization from, e.g., ether-alcohol mixture.

Other 5-substituted pyrimideinediones such as bromo, iodo, alkylamino, hydroxymethyl and the like may be prepared by the methods described in *J. Med. Chem.*, 26(2):156 (1983). The compounds wherein the 5-position is substituted by a halovinyl group may be prepared by the method described in European Pat. No. 104,066.

Using the methods described above the following compounds may be prepared:

3-(2,4-dioxo-5-methylprimidin-1-yl)-4-fluoro-5-hydroxymethylcyclopentane-1,2-diol;

3-(2,4-dioxo-5-methylpyrimidin-1-yl)-4,4-difluoro-5-hydroxymethylcyclopentane-1,2-diol;

3-(2,4-dioxo-5-methylpyrimidin-1-yl)-4-hydroxy-5-hydroxymethylcyclopentane-1,2-diol;

3-(2,4-dioxo-5-methylpyrimidin-1-yl)-4-oxo-5-hydroxymethylcyclopentane-1,2-diol;

3-(2,4-dioxopyrimidin-1-yl)-4-fluoro-5-hydroxymethylcyclopentane-1,2-diol;

3-(2,4-dioxopyrimidin-1-yl)-4,4-difluoro-5-hydroxymethylcyclopentane-1,2-diol;

3-(2,4-dioxopyrimidin-1-yl)-4-hydroxy-5-hydroxymethylcyclopentane-1, 2-diol;

3-(2,4-dioxopyrimidin-1-yl)-4-oxo-5-hydroxymethylcyclopentane-1,2diol;

3-(2,4-dioxo-5-fluoropyrimidin-1-yl)-4-fluoro-5-hydroxymethylcyclopentane-1, 2-diol;

3-(2,4-dioxo-5-fluoropyrimidin-1-yl)-4,4-difluoro-5-hydroxymethylcyclopentane-1,2-diol;

3-(2,4-dioxo-5-fluoropyrimidin-1-yl)-4-hydroxy-5-hydroxymethylcyclopentane-1,2-diol;

3-(2,4-dioxo-5-fluoropyrimidin-1-yl)-4,4-oxo-5-hydroxymethylcyclopentane-1,2-diol;

3-(4-amino-2-oxopyrimidin-1-yl)-4-fluoro-5-hydroxymethylcyclopentane-1,2-diol;

3-(4-amino-2-oxopyrimidin-1-yl)-4,4-difluoro-5-hydroxymethylcyclopentane-1,2-diol;

3-(4-amino-2-oxopyrimidin-1-yl)-4-hydroxy-5-hydroxymethylcyclopentane-1,2-diol; and 3-(4-amino-2-oxopyrimidin-1-yl)-4-oxo-5-hydroxymethylcyclopentane-1,2-diol.

Compounds of formula (I) wherein A and C are both hydroxy and C is in the β-position may be prepared by reacting the compound wherein A and C are in the α-position with a silylating reagent by the method described in *Tetrahedron Letters*, 157–4 (1980). The silyl protected compound is then reacted with trifluoromethanesulfonyl chloride followed by reaction with salts such as sodium acetate by the methods described in *Tetrahedron Letters*, 4341–44 (1978). The acetate group is removed with methanolic ammonia.

Compounds of formula (I) wherein A is hydroxy and C is hydrogen may be prepared from the above silyl protected compound by reaction with 1,1-diimidazolylthiocarbonyl followed by reduction with tributyl tin hydride.

For example, the following compounds may be prepared by the methods discussed above.

3-(2,4-dioxo-5-iodopyrimidin-1-yl)-4-fluoro-5-hydroxymethylcyclopentan-1-ol;

3-(2,4-dioxo-5-iodopyrimidin-1-yl)-4,4-difluoro-5-hydroxymethylcyclopentan-1-ol;

3-(2,4-dioxo-5-iodopyrimidin-1-yl)-4-hydroxy-5-hydroxymethycyclopentan-1-ol;

3-(2,4-dioxo-5-iodopyrimidin-1-yl)-4-oxo-5-hydroxymethylcyclopentan-1-ol;

3-(2,4-dioxo-5-fluoropyrimidin-1-yl)-4-fluoro-5-hydroxymethylcyclopentan-1-ol;

3-(2,4-dioxo-5-fluoropyrimidin-1-yl)-4,4-difluoro-5-hydroxymethylcyclopentan-1-ol;

3-(2,4-dioxo-5-fluoropyrimidin-1-yl)-4-hydroxy-5-hydroxymethylcyclopentan-1-ol;

3-(2,4-dioxo-5-fluoropyrimidin-1-yl)-4-oxo-5-hydroxymethylcyclopentan-1-ol;

3-(2,4-dioxo-5-trifluoromethylpyrimidin-1-yl)-4-fluoro-5-hydroxymethylcyclopentan-1-ol;

3-(2,4-dioxo-5-trifluoromethylpyrimidin-1-yl)-4,4-difluoro-5-hydroxymethylcyclopentan-1-ol;

3-(2,4-dioxo-5-trifluoromethylpyrimidin-1-yl)-4-hydroxy-5-hydroxymethylcyclopentan-1-ol;

3-(2,4-dioxo-5-trifluoromethylpyrimidin-1-yl)-4-oxo-5-hydroxymethylcyclopentan-1-ol;

3-(2,4-dioxo-5-(2-bromovinyl)pyrimidin-1-yl)-4-fluoro-5-hydroxymethylcyclopentan-1-ol;

3-(2,4-dioxo-5-(2-bromovinyl)pyrimidin-1-yl)-4,4-difluoro-5-hydroxymethylcyclopentan-1-ol;

3-(2,4-dioxo-5-(2-bromovinyl)pyrimidin-1-yl)-4-hydroxy-5-hydroxymethylcyclopentan-1-ol;

3-(2,4-dioxo-5-(2-bromovinyl)pyrimidin-1-yl)-4-oxo-5-hydroxymethylcyclopentan-1-ol;

3-(2,4-dioxo-5-(2-iodovinyl)pyrimidin-1-yl)-4-fluoro-5-hydroxymethylcyclopentan-1-ol;

3-(2,4-dioxo-5-(2-iodovinyl)pyrimidin-1-yl)-4,4-difluoro-5-hydroxymethylcyclopentan-1-ol;

3-(2,4-dioxo-5-(2-iodovinyl)pyrimidin-1-yl)-4-hydroxy-5-hydroxymethylcyclopentan-1-ol; and 3(2,4-dioxo-5-(2-iodovinyl)pyrimidin-1-yl)-4-oxo-5-hydroxymethylcyclopentan-1-ol.

Compounds of formula (I) wherein B is 2,4-dioxo-5-trifluoromethylpyrimidin-1-yl or 4-amino-2-oxo-5-trifluoromethylpyrimidin-1-yl may be prepared by reacting compound of formula (IX) with trifluoroacrylonitrile which is prepared by the method described in *J. Med. Chem.*, 7(1):1–5 (1964). The resulting compound is reacted with cyanic acid to form compound of formula (X) wherein R is 1-(2-cyanoethyl)-1-trifluoromethylaminocarbonyl as is described in *J. Heterocyclic Chem.*, 527–535 (1970). This compound is cyclized with a base such as sodium methoxide to form a compound of formula (XI) followed by reaction with bromine. The bromine compound is dehydrobromenated using a base such a sodium hydroxide in methanol. The benzyl group and the isopropylidene are removed by the methods described above. Compound of formula (I) wherein B is 4-amino-2-oxo-5-trifluoromethylpyrmidin-1-yl is converted to the compound of formula (I) wherein B is 2,4-dioxo-5-trifluoromethylpyrimidin-1-yl by treatment with nitrous acid.

The compound of formula (XIII) are prepared from the compounds of formula (I) wherein B is a substituted pyrimidinyl and the hydroxy groups in the 1 and 2 positions of the cyclopentyl ring are in the down position by the method described in U.S. Pat. No. 3,709,874. The above compound of formula (I) is reacted with an α-acyloxy acid halide such as 2-acetyloxy-3-methylbutanoye chloride in an inert organic solvent at 0° to 150° C. for about 5 minutes to 10 hours, preferably at 20° C. to 100° C. for 5 minutes to one hour. The compound of formula (XIV) is recovered by, e.g., chromatography. The α-acyloxy acid halide is prepared by reacting an α-hydroxy acid with an acid chloride. The resulting α-acyloxy acid is then treated with thionyl chloride or oxalyl chloride to form the α-acyloxy acid chloride.

The following compounds, for example, may be prepared by the above method:

| X | Y | Z | Z' |
|---|---|---|---|
| oxygen | iodo | fluoro | hydrogen |
| oxygen | iodo | fluoro | fluoro |
| oxygen | methyl | fluoro | hydrogen |
| oxygen | methyl | fluoro | fluoro |
| oxygen | trifluoromethyl | fluoro | hydrogen |
| oxygen | trifluoromethyl | fluoro | fluoro |
| imino | iodo | fluoro | hydrogen |
| imino | iodo | fluoro | fluoro |

The compound of formula (XIII) not only possesses antiviral activity but is also useful as an intermediate for the preparation of the compound of formula (I) wherein B is a substituted pyrimidinyl and the hydroxy group at position-1 is in the down position and the hydroxy group at position-2 is in the up position by treating compound of formula (XIII) with a base such as sodium hydroxide.

Another method for preparing the compounds of the invention is by reacting the compound of formula (VI) with a purine derivative. For example, for compounds of formula (I) wherein B is guanine, compound of formula (VI) in a solvent such as dimethylformamide is reacted with the sodium salt of guanine.

Compounds of formula (I) exist as optical isomers. The compounds may be prepared as their racemic mixture or may be separated into their optical isomers by various methods. One such method is by resolving the racemic mixture of the intermediate of formula (VIII) and then reacting each isomer as described above to prepare optical isomers of compound of formula (I).

Racemic compound of formula (VIII) is reacted with an optically active acid chloride such as 6-methoxynaphth-2-yl-2-propanoyl chloride in a solvent such as dichloromethane containing pyridine. The solution is stirred for 2 to 8 hours, preferably for 3 to 6 hours, at room temperature. The diasteromers of compound of formula (VIII) are separated by chromatography on silica gel. The optical isomers of formula (VIII) is prepared by basic hydrolysis. The diastereoisomer in a solvent such as tetrahydrofuran and a base such as sodium hydroxide is heated at reflux for 2 to 12 hours, preferably for 2 to 8 hours. The solution is evaporated to dryness. The optical isomers of formula (VIII) is recovered by chromatography.

The following examples are illustratrative of the methods and compositions of the present invention. They should not be construed as limitative thereof in any manner.

PREPARATION I

Benzyl chloromethyl ether (208 mL) was added dropwise over 30 minutes to a mechanically stirred suspension of thallium cyclopentadiene (475 g) in ether (450 ml). The resulting suspension was mechanically stirred at −20° C. for an additional 18 hours and then filtered with the filtrate flask precooled to −20° C. The filtrate was evaporated at 0° C./1 Torr to give the alkylated cyclopentadiene as a clear oil. The oil was dissolved in cold (−20° C.) methanol, and transferred to a −5° C. solution of thiourea (126 g), sodium acetate (2.8 g) and Rose Bengal (2–8 g) in methanol (5 gal, saturated with oxygen). The solution was irradiated at −5° C. for 9 hours with a 400 watt mercury immersion lamp with continuous bubbling of oxygen into the solution. The lamp was cooled with a 0° C. solution of aqueous $Na_2Cr_2O_7$. The resulting solution was evaporated by a rotary evaporator to a dark brown oil which was dissolved in ethyl acetate, washed with water and evaporated to a light brown oil. The oil was chromatographed over silica gel to give 197 g of 2β-benzyloxymethyl-1α,3α-dihydroxycyclopent-4-ene, m.p. 47°–48° C.

PREPARATION II

A solution of 2β-benzyloxymethyl-1α,3α-dihydroxycyclopent-4-ene (0.22 g) and m-chloroperbenzoic acid (0.18 g) in dichloromethane (10 mL) was stirred for 36 hours at room temperature. After filtration, the filtrate was concentrated using a rotary evaporator and chromatographed on silica gel eluting with ethyl acetate-hexane (8:2) to obtain 0.18 g of the colorless crystals of 2β-benzyloxymethyl-1α,3α-dihydroxy-4α,5α-epoxycyclopropane, m.p. 170°–171° C.

PREPARATION III

To a stirred solution of 2β-benzyloxymethyl-1α,3α-dihydroxy-4α,5α-epoxycyclopentane (0.472 g) in dry dimethylformamide (20 mL) was added sodium azide (0.910 g). The mixture was maintained at 100° C. on an oil bath for 12 hours. The dimethylformamide was evaporated under vacuum and the concentrate was partitioned between ethyl acetate-water (1:1). The ethyl acetate layer was concentrated after drying $(Na_2SO_4)$ to yield a red oil (0.44 g). The oil was purified on a silica gel column eluting with ethyl acetate-hexane (1:1) to yield 0.35 g of the pure 5β-benzyloxymethyl-1α,2α,4α-trihydroxy-3β-azidocyclopentane as a colorless liquid.

$^{13}$C NMR (75.453 MHz, CDCl$_3$) 137.73, 128.57, 127.95, 127.74 (phenyl), 75.05 (C-3), 74.20 (C-4), 73.55 (benzylic), 71.97 (C-2 ), 71, 68 (C-1), 70.21 (C-6), 51.81. (C-5).

PREPARATION IV

Preparation of Compound of Formula (VIII)

To a stirred solution of the azido triol from Preparation III (0.558 g) and 2,2-dimethoxypropane (1mL) in dry acetone (10 mL) was added 70% perchloric acid (0.1 mL). The resulting solution was stirred for 45 minutes at room temperature followed by the dropwise addition of ammonium hydroxide to neutralize the solution. The solvents were removed at the rotary evaporator. The crude concentrate was dissolved in ethyl acetate, washed twice with water and brine. The organic layer was concentrated at the rotary evaporator to yield a dark brown liquid (0.62 g). The brown liquid was purified by column chromatography [silica gel eluting with hexane-ethyl acetate (8:2)] to yield 0.54 g of 3β-azido-4α-hydroxy-5β-benzyloxymethyl-1α,2α-isopropylidenedioxycyclopentane as a colorless liquid.

$^{13}$C NMR (75.453 MHz, CDCl$_3$) 137.76, 128.57, 127.96, 127.76 (phenyl), 113.12 (OCO), 81.30 (C-2), 77.87 (C-1, C-4), 73.58 (benzylic), 72.23 (C-3), 69.54 (C-6), 50.28 (C-5), 27.25 (CH$_3$), 24.86 (CH$_3$).

PREPARATION V

Preparation of Compound of Formula (IX) wherein is hydroxy and Z' is hydrogen

Hydrogen gas was added to a solution of 3β-azido-4α-hydroxy-5β-benzyloxymethyl-1α,2α-isopropylidenedioxycyclopentane (0.31 g) and palladium on calcium carbonate (0.75 g) in methanol (15 mL) from a rubber balloon attached to the flask. After the solution was stirred for 12 hours, the catalyst was filtered off and washed with hot methanol (2×25 mL). The washings were combined with the filtrate and the resulting solution was concentrated. The concentrate was chromatographed over silica gel eluting with ethyl acetate. After the solvent was removed by rotary evaporator, light yellow crystals (0.26 g) of 3β-amino-4α-hydroxy-5β-benzyloxymethyl-1α,2α-isopropylidenedioxycyclopentane were obtained. Recrystallization with hexane-ethyl acetate gave pure 3β-amino-4α-hydroxy-5β-benzyloxymethyl-1α,2α-isopropylidinedioxycyclopentane, m.p. 106°–107° C.

PREPARATION VI

Preparation of Compound of Formula (X) wherein Z is hydroxy, Z' is hydrogen and R is 5-amino-6-chlor-O-pyrimidin-4-yl)

A solution of 3β-amino-4α-hydroxy-5β-benzyloxymethyl-1α,2αisopropylidenedioxycyclopentane (0.293 g), pyridine (0.08 g) in N-methyl-2-pyrrolidone (25 mL) and 5-amino-4, 6-dichloropyrimidine (0.164 g) was stirred at 180° C. for 12 hours. The solvent was removed by rotary evaporator and the concentrate was dissolved in ethyl acetate (25 mL). The ethyl acetate solution was washed with water (25 mL), dried (Na$_2$SO$_4$) and concentrated by a rotary evaporator to yield 0.44 g of a brown oil. This oil was chromatographed over silica gel eluting with ethyl acetate-hexane (1:1) to yield 0.285 g of 3β-(5-amino-6-chloropyrimidin-4-yl)amino-4α-hydroxy-5β-benzyloxymethyl-1α,2α-isopropylidenedioxycyclopentane, as light yellow crystals, m.p. 108°–109° C.

PREPARATION VII

Preparation of Compound of Formula (XI) wherein Z is hydroxy, Z' is hydrogen and B is 6-chloropurin-9-yl 3β-(5-Amino-6-chloropyrimidin-3-yl)amino-4α-hydroxy-5β-benzyloxymethyl-1α,2α-isopropylidenedioxycyclopentane-1α,2α-acetonide (0.210 g) in diethoxymethylacetate (5 mL) was heated at 100° C. for 1 hour under nitrogen atmosphere. After concentration of the solution by a rotary evaporator, toluene and p-toluenesulphonic acid (2 crystals) were added and the solution was stirred at room temperature for 1 hour. After removal of the solvent by a rotary evaporator, the crude concentrate was chromatographed over silica gel eluting with methylene chloride-methanol (9.5:0.5) to give 0.215 g of 3β-(6-chloropurin-9-yl)-4α-hydroxy-5β-benzyloxymethyl-1α,2α-isopropylidenedio xycyclopentane which after recrystallization from hexane-ethyl acetate (8:2) gave a colorless crystalline solid, m.p. 190°–191° C.

PREPARATION VIII

Preparation of Compound of Formula (XI) wherein Z is hydroxy, Z' is hydrogen and B is 6-aminopurin-9-yl)

A solution of 3β-(6-chloropurin-9-yl)-4α-hydroxy-5β-benzyloxymethyl-1α,2α-isopropylidenedioxycyclopentane (0.215 g) in anhydrous methanolic ammonia (10 mL) was heated for 48 hours at 60° C. in a lightly sealed flask. The solvent was removed by a rotary evaporator and the resultant white solid was recrystallized from ethyl acetate-methanol (9:1). 3β-(6-Aminopurin-9-yl)-4α-hydroxy-5β-benzyloxymethyl-1α,2α-iso- propylidenedioxycyclopentane (0.15 g) was obtained as a colorless solid, m.p. 236°–237° C.

PREPARATION IX

Preparation of Compound of Formula (XII) wherein Z is hydroxy, Z' is hydrogen and B is 6-aminopurin-9-yl A solution of 3β-(6-aminopurin-9-yl)-4α-hydroxy-5β-benzyloxymethyl-1α,2α-isopropylidenedioxycyclopentane (8 mg) and cyclohexene (1 mL) in ethanol (2 mL) containing palladium hydroxide on carbon (3 mg) was refluxed for 6 hours. The catalyst was removed by filtration and washed with hot ethanol (2×10 mL). The washings were combined with the filtrate and concentrated by a rotary evaporator. The concentrated filtrate was purified by silica gel chromatography eluting with methylene chloride-methanol (8:2). 3β-(6-Aminopurin-9-yl)-4α-hydroxy-5β-hydroxymethyl-1α,2α-isopropylidenedioxycyclopentane (64 mg) as colorless crystals were obtained, m.p. 238°–239° C.

PREPARATION X

To a solution of 3β-azido-4α-hydroxy-5β-benzyloxymethyl-1α,2α-isopropylidenedioxy-cyclopentane (0.40 g) and pyridine (0.12 g) in dichloromethane (10 mL) was added trifluoromethanesulfonic anhydride (0.31 g) in dichloromethane (2 ml). The resulting solution was stirred at room temperature under nitrogen atmosphere for 1 hour. The solution was diluted with 20 mL of dichloromethane, washed with 20 mL of 0.1 N NaHCO$_3$ and water. From the dichloromethane layer was obtained 3β-azido-4α-trifluoromethanesulfoxy-5β-benzyloxymethl-1α,2α-isopropylidenedioxycyclopentane (0.50 g).

PREPARATION XI

Preparation of Compound of Formula (IX) wherein Z is fluoro and Z' is hydrogen

A. A solution containing 3β-azido-4α-trifluoromethane-sulfonyloxy-5β-benzyloxymethyl-1α,2α-isopropylidene-dioxycyclopentane (0.30 g) from preparation (X) and tris(dimethylamino)sulfonium difluorotrimethyl-silicate (TASF) (0.22 g) in dry tetrahydrofuran (5 mL) was stirred under nitrogen atmosphere for 12 hours under reflux. The solution was diluted with ethyl acetate (20 mL), washed with water and dried with Na$_2$SO$_4$. The ethyl acetate layer was concentrated using a rotary evaporator and chromatographed over silica gel eluting with hexane-ethyl acetate (8:2). 3β-Azido-4β-fluoro-5β-benzyloxymethyl-1α,2α-isopropylidenedioxy-cyclopentane was isolated as a clear liquid (0.20 g). $^1$H-NMR (CHCl$_3$) 7.35–7.25 (m, 5H, phenyl), 5–20 (t, J=Hz, 3 Hz, 52 Hz, 1 H, H-4), 4.68 (t, J=6 Hz, 1H, H-2), 4.56 (S, 2H, benzylic), 4.48 (t, J=66 Hz, 1H, H-1), 3.75 (m, 1H, H-3), 3.66 (d, J=4 Hz, 2 H, H-6) and 2.50 (m, 1H, H-5).

B. To a solution containing 3β-azido-4β-fluoro-5β-benzyloxymethyl-1α,2α-isopropylidenedioxycyclopentan e(0.09 g) in methanol (5 mL) was added palladium on calcium carbonate (0.009 g) and the suspension was stirred under positive hydrogen pressure for 6 hours. After removal of the catalyst by filtration, the solution was concentrated by rotary evaporator and chromatographed over silica gel eluting with methylenechloride-methanol (9.8:02) to obtain 3β-amino-4β-fluoro-5β-benzyloxymethyl-1α,2α-isopropylidenedioxy cyclopentane was obtained as a viscous oil, $^1$H NMR (300 MHz, CDCl$_3$) 7.2–7.4 (m, SH, phenyl), 5.0 (ddd J=3.1, 3.1 and 53 Hz, 1H, H-4), 4.56 (s, 2H, benzylic), 4.43 (dd J=7.2, 7.2 Hz, 1H, H-3'), 4.35 (dd J=7.2 Hz, 1H, H-2'), 3.66 (d, J=7.9 Hz, 2H, H-6), 3.30 (ddd, J=5.6, 5.6 and 29.9 Hz, 1H, H-3), 2.60 - 2.35 (m, 1H, H-5), 1.54 (broad singlet, 2H, NH$_2$, disappears on D$_2$O), 1.50 and 1.30 (2×s, 3H each, 2×CH$_3$).

PREPARATION XII

Preparation of Compound of Formula (X) wherein Z is fluoro, Z' is hydrogen and R is 5-amino-6-chloro-pyrimidin-4-yl A solution containing 3β-amino-4β-fluoro-5β-benzyloxymethyl-1α,2α-isopropylidenedioxycyclopentane (0.6 g), 5-amino-4, 6-dichloropyrimidine (0.66 g) and triethylamine (1.60 g) in n-butanol (10 mL) was refluxed for 48 hours under nitrogen atmosphere. After cooling to room temperature, the triethylamine hydrochloride was removed by filtration. The filtrate was concentrated using a rotary evaporator and the concentrated filtrate partitioned between ethyl acetate and water. The ethyl acetate layer was chromatographed over silica gel eluting with hexane-ethyl acetate (6:4). After evaporation of the solvent 3β-(5-amino-6-chloropyrimidin-4-yl)amino-4β-fluoro-5β-benzyloxymethyl-1α,2α-isopropylidenedioxy-cyclopentane (0.55 g) was obtained as colorless crystals, m.p. 172°-173° C.

PREPARATION XIII

Preparation of Compound of Formula (XI) wherein Z is fluoro, Z' is hydrogen and B is 6-chloropurin-9-yl)

A solution of 3β-(5-amino-6-chloropyrimidin-4-yl)-amino-4β-fluoro-5β-benzyloxymethyl-1α,2α-isopropyli-denedioxycyclopentane (0.42 g) in diethoxymethylacetate (4 mL) was heated at 100° C. on as oil bath for 12 hours. The solution was concentrated by a rotary evaporator and chromatographed over silica gel, eluting with hexane-ethyl acetate (8:2). After evaporation of the solvent 3β-(6-chloropurin-9-yl)-4β-fluoro-5β-benzyloxymethyl-1α,2α-isopropylidenedioxycyclopentane (0.35 g) as a light yellow gummy solid. $^1$H NMR (300 MHz, CDCL$_3$) 8.77 (s, 1H, H-2), 8.34 (d, J=2.3Hz, 1H, H-8), 7.33-7.26 (m, 5H, phenyl), 5.23 (ddd, J=3.1, 3.1 and 46.12Hz), 5.10-5.30 (M, 2H, H-3* and H-2* 4.66 (dd, J=7.5 Hz, 1H, H-1*), 4.59 (S, 2H, benzylic), 3.75 (d, J=8.0Hz, 2H, H-6*) 3.90-3.70 (M, 1H, H-5*), 1.59 and 1.35 (2×S, 3H each, 2×CH$_3$). *refers to the cyclopentane ring.

PREPARATION XIV

Preparation of Compound of Formula (XI) wherein Z is fluoro, Z' is hydrogen and B is 6-aminopurin-9-yl A solution of 3β-(6-chloropurin-9-yl)-4β-fluoro-5β-benzyloxymethyl-1α,2α-isopropylidenedioxyclyclopentane (2.0 g) in methanolic ammonia (20 mL) in a bomb reactor was kept at 90° C. for 6 hours. The solution was concentrated by a rotary evaporator and the resulting solid was dissolved in methanol and chromatographed over silica gel eluting with methylene chloride-methanol (9.9:0.1). 3β-(6-Aminopurin-9-yl)-4β-fluoro-5β-benzyloxy-methyl-1α,2α-isopropylidenedioxycyclopentane (1.13 g) was obtained as a colorless solid, m.p. 178°-179° C.

PREPARATION XV

Preparation of Compound of Formula (XII) wherein Z is fluoro, Z' is hydrogen and B is 6-aminopurin-9-yl A solution of 3β-(6-aminopurin-9-yl)-4β-fluoro-5β-benzyloxymethyl-1α,2α-isopropylidenedioxycyclopentane (0.8 g), palladium hydroxide on carbon (0.08 g) and cyclohexene (6 ml) in ethanol (10 ml) was refluxed for 48 hours. The catalyst was filtered off and the filtrate was concentrated by a rotary evaporator. The concentrated filtrate was chromatographed over silica gel eluting with methylene chloride-methanol (9.5:0.6). After recrystallization from hexane-ethylacetate 3β-(6-aminopurin-9-yl)-4β-fluoro-5β-hydroxymethyl-1α,2α-isopropylidenedioxycyclopentane (0.50 g) was obtained as colorless crystals, m.p. 132°-133° C.

PREPARATION XVI

Preparation of Compound of Formula (VIII) wherein the 4-hydroxy is in the up (β) position A solution containing 3β-azido-4α-trifluoromethanesulfonoxy -5β-benzyloxymethyl-1α,2α-isopropylidenedioxycyclopentane from Preparation (X) (0.5 g) and lithium fluoride (0.52 g) in dimethylsulfoxide (0.5 g) and stirred for 4 hours at room temperature. The reaction mixture was diluted with ethylacetate (25 ml) and washed with water (2×15 mL). The ethyl acetate layer was chromatographed over silica gel eluting with hexane-ethyl acetate (8:2) and 3β-azido-4-β-hydroxy-5β-benzyloxymethyl-1α,2α-isopropylidenedioxy (0.30 g) was obtained as a clear oil.

PREPARATION XVII

Preparation of Optically Active Compounds of Formula (VIII)

A. To a solution of racemic 3β-azido-4α-hydroxy-5β-benzyloxymethyl-1α,2α-isopropylidenedioxycyclopentane (0.32 g) in dichloromethane (10 mL) containing pyridine (1 mL) was added the 6-methoxynaphtyh-2-yl-2-propanoyl chloride in 3 mL of dichloromethane. The resulting solution was stirred for 4 hours at room temperature and then diluted with 40 mL of dichloromethane. This solution was washed with 0.1N NaHCO$_3$(2×20 mL), water (10 mL) and brine (10 mL). The dichloromethane layer was separated, concentrated and dried (Na$_2$SO$_4$). The resulting oil was chromatographed over silica gel eluting with hexane-toluene-ethyl acetate (8.5:1.0:0.5) and each of the disasteromers of the ester was obtained as a light yellow oil (0.211 g).
Diasteromer-1 [α]$_D$$^{25}$ 54.6° (C CHCl$_3$).
Diasteromer-2 [α]$_D$$^{25}$ −31.8° (C CHCl$_3$).

B. A solution of diasteromer 2 from Part A (5.0 g) and sodium hydroxide (0.40 g) in tetrahydrofuran (50 mL) was heated at reflux for 4 hours. The solution was evaporated to dryness using a rotary evaporator. The residue was dissolved in ethyl acetate, washed with saturated aqueous NaHCO$_3$, dried over Na$_2$SO$_4$and evaporated to dryness. The residue was dissolved inethyl acetate and purified by chromatography over silica gel eluting with ethyl acetate-hexane (1:9) to give 2.54 g of (−)-3β-azido-4α-hydroxy-5β-benzyloxymethyl-1α,2α-isopropylidenedioxycyclopentane as a clear oil.
[α]$_D$$^{25}$ −26.0° (C 0.3, CHCl$_3$).
Similarly, (+)-3β-azido-4α-hydroxy-5β-benxyloxymethyl-1α,2α-isopropylidenedioxycyclopentane using the above procedure was obtained from diasteromer-1.

$[\alpha]_D^{25}$ 26.1° (C 0.28, CHCl$_3$).

PREPARATION XVIII

A solution of 3β-(6-aminopurin-9-yl)-4α-hydroxy-5β-benzyloxymethyl-1α,2α-isopropylidenedioxycyclopentane (35 mg) and 1, 1-diimidazolylthiocarbonyl (27 mg) in dimethylformamide (0.2 mL) was heated at 75° C. for 3 hours. The solution was concentrated by a rotary evaporator and the residue was chromatographed over silica gel eluting with methanol-methylene chloride (1:14) to yield 27.4 mg of 3β-(6-aminopurin-9-yl)-4α-(1-imidazolylthiocarbonyloxy)-5β-benzyloxymethyl-1α,2α-isopropylidenedioxycyclopentane as a white solid, m.p. 163°-165° C.

PREPARATION XIX

Preparation of Compound of Formula (IX) wherein Z and Z' are both hydrogen

A. A solution of (−)-3β-azido-4α-hydroxy-5β-benzyloxymethyl-1α,2α-isopropylidenedioxycyclopentane (1.76 g), trifluoromethanesulfonic anhydride (1.68 g) and pyridine (0.56 g) in dichloromethane (15 mL) was kept at room temperature for 1 hour. The solution was washed with water and saturated aqueous NaHCO$_3$, dried over Na$_2$SO$_4$ and evaporated by a rotary evaporator to give the trifluoromethanesulfonate as a brown oil. A solution of the residue and lithium iodide (0.9 g) in dimethylformamide (20 mL) was kept at room temperature for 1 hour. The solution was then diluted with ethyl acetate, washed with water, dried over Na$_2$SO$_4$ and evaporated to dryness. The residue was purified by chromatography to give 1.65 g of (−)-3β-azido-4β-iodo-5β-benzyloxymethyl-1α,2α-isopropylidenedioxycyclopentane as a yellow oil. $[\alpha]_D^{25}$ −33.6° C. (C 0.3, CHCl$_3$).

Similarly, using the above procedure (+)-3β-azido-4α-iodo-5β-benzyloxymethyl-1α,2α-isopropylidenedioxycyclopentane was obtained from the (+)-azido hydroxy acetonide $[\alpha]_D^{25}$ 35.6° C. (C 0.3, CHCl$_3$).

B. A mixture of (−)-3β-azido-4β-iodo-5β-benzyloxymethyl-1α,2α-isopropylidenedioxycyclopentane and 10% palladium on carbon (0.15 g) in methanol (25 mL) was shaken on a Parr apparatus under 20 psi of hydrogen at room temperature for 6 hours and then filtered through Celite. The filtrate was evaporated to dryness using a rotary evaporator and the residue was dissolved in methanol and chromatographed over silica gel eluting with methanol-methylene chloride (0.5:9.5) to give 0.78 g of (−)-3β-amino-5β-benzyloxymethyl-1α,2α-isopropylidenedioxycyclopentane as a yellow oil. $[\alpha]_D^{25}$ −2.9° (C 0.8, CHCl$_3$).

Similarly, using the above procedure (+)-3-amino-5-benzyloxymethyl-1α,2α-isopropylidenedioxycyclopentane was obtained from the (+)-azido iodo acetonide. $[\alpha]_D^{25}$ 2.80° (C 0.49, CHCl$_3$).

PREPARATION XX

A solution of (−)-3β-amino-5β-benzyloxymethyl-1α,2α-isopropylidenedioxycyclopentane (0.60 g) in 80% aqueous acetic acid (5 mL) was heated at 80° C. for 1 hour and then evaporated to dryness using a rotary evaporator. The magnetically stirred solution of the residue in ammonia (15 mL) at −78° C. was treated with sodium and then quenched with ammonium chloride. The solution was then evaporated to dryness. The residue dissolved in ion-free water was purified on a cation exchange resin (Dowex AG 50 W-x8, H+ form) eluting with 0.07 M ammonium hydroxide to give 0.20 g of (−)-3β-amino-5β-hydroxmethylcyclopentane-1α,2α-diol as a clear oil. $[\alpha]_D^{25}$ −10.3° (C 0.3, CHCl$_3$).

Similarly, using the above procedure (+)-3β-amino-5β-hydroxymethylcyclopentane-1α,2α-diol was obtained from the (+) amino acetonide.

$[\alpha]_D^{25}$ 10.3° (C 0.32, H$_2$O).

EXAMPLE 1

Preparation of Compound of Formula (I) wherein Z is hydroxy, Z' is hydrogen and B is 6-aminopurin-9-yl 3β-(6-Aminopurin-9-yl)-4α-hydroxy-5β-hydroxymethyl-1α,2α-isopropylidenedioxycyclopentane (0.16 g) was heated at 65° C. in 70% acetic acid for 30 minutes and concentrated by rotary evaporator. The resulting colorless crystals were recrystallized from ethyl acetate-methanol to yield 0.12 g of 3β-(6-aminopurin-9-yl)-5β-hydroxymethylcyclopenentane-1α,2α,4α-triol, m.p. 244°-245° C.

EXAMPLE 2

Preparation of Compound of Formula (I) wherein Z is fluro, Z' is hydrogen and B is 6-aminopurin-9-yl A solution of 100 mg of 3β-(6-aminopurin-9-yl)-4β-fluoro-5β-hydroxymethyl-1α,2α-isopropylidenedioxycyclopentane in 10% aqueous hydrochloric acid (3 mL) was warmed to 70° C. for a few minutes and the solvents were then removed by a rotary evaporator. The resulting colorless gelatinous material was triturated with ammonium hydroxide and concentrated. The colorless solid was crystallized from hot water to give 3β-(6-aminopurin-9-yl)-4β-fluoro-5β-hydroxymethylcyclopentane-1α,2α-diol (0.08 g) colorless crystals, m.p. 280°-281° C.

EXAMPLE 3

A solution of N$^6$-benzoyladenine (0.35 g) and sodium hydride (0.035 g) in anhydrous dimethylformamide (5 ml) was kept at 100° C. for 45 minutes. To this solution was added 5β-benzyloxymethyl-1α,2α-dihydroxy-4α,5α-epoxy cyclopentane and the resulting solution was stirred at 100° C. for 12 hours. The solvent was removed at the rotary evaporater and the resulting solid mass was partitioned between water and n-butyl alcohol-methylene chloride (1:9). The organic layer was separated, dried with anhydrous sodium sulphate and concentrated to yield 0.12 g of a red brown viscous liquid which on preparative plate silica gel chromatography (methylene chloride-methanol (9:1) as eluant), yielded 3β-(6-aminopurin-9-yl)-4α-hydroxy-5β-benzyloxymethylcyclopentane-1α,2α-diol (0.03 g) as a yellow solid, mp. 165°-6° C.

The benzyl group is removed by reduction with palladium hydroxide on carbon to form 3β-(6-aminopurin-9-yl)-4α-hydroxy-5β-hydroxy-methylcyclopentane-1α,2α-diol.

Simiarly, using the above procedure 3β-(2-amino-6-hydroxypurin-9-yl)-4α-hydroxy-5β-hydroxymethylcyclopentane-1α,2α-diol is prepared.

EXAMPLE 4

The following example illustrates the preparation of representative pharmaceutical formulations containing an active compound of Formula (I) or compounds of formula (XIII).

| A. Topical Formulation | |
| --- | --- |
| Active compound | 0.2-2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water qs | 100 ml |

All of the above ingredients, except water, are combined and heated at 60° C. with stirring. A sufficient quantity of water at 60° C. is then added with vigorous stirring to provide 100 g of the cream formulation which is then cooled to room temperature.

The following formulation is useful for intraperitoneal and intramuscular injection.

| B. IP and IM Formulation | |
| --- | --- |
| Active compound | 0.5 g |
| Propylene glycol | 20 g |
| Polyethylene glycol | 20 g |
| Tween 80 | 1 g |
| 0.9% Saline solution qs | 100 ml |

The active compound is dissolved in propylene glycol, polyethylene glycol 400 and Tween 80. A sufficient quantity of 0.9% saline solution is then added with stirring to provide 100 ml of the I.P or I.M solution which is filtered through a 0.2 micron membrane filter and packaged under sterile conditions.

The following formulation is useful for intravenous injection.

| C. I.V. Formulation | |
| --- | --- |
| Active compound | 0.1 g |
| Polysorbate 80 | 0.1 g |
| Propylene glycal or polyethylene glycol 400 | 3.0 g |
| Water qs | 100 ml |

The active compound is added to a solution of polysorbate 80 and propylene glycol or polyethylene glycol 400 in 20ml of water and mixed. The resulting solution is diluted with water to 100 ml and filtered through the appropriate 0.2 micron membrane filter.

| D. Tablet Formulation | |
| --- | --- |
| | Parts by weight |
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg of active compound) with an appropriate tabletting machine.

EXAMPLE 5

The exceptional antiviral activity of the compound of the invention is illustrated by the following assay procedures:

The Herpes simplex virus 2 strain G for infection is prepared in HEp-2 cell cultures. Virus is adsorbed for 1 hour, fresh media is placed on the cells, and they are incubated at 35° C. until all cells were infected. The cell suspension is frozen at −70° C., thawed, and centrifuged to remove cell debris. The supernatant fluid is aliquoted and stored frozen at −70° C. until use. A $10^{6.7}$ dilution of the supernatant fluid produces a 50% cell culture infective dose ($CCID_{50}$) in HEp-2 cells and a $10^{3.7}$ dilution produces a 50% lethal challenge ($LC_{50}$) in mice.

Groups of 20 Swiss Webster female mice (15-17 gm), are challenged by intraperitoneal route using 0.2 ml of EMEM containing 10 $LC_{50}$/mouse of virus. Mice challenged with $10^{0.5}$ more or less virus than the 10 $LD_{50}$ challenge serves as a virulence control to assure the model is working properly.

Treatment with test compounds begins 6 hours post-challenge. The mice, divided into groups of 20, are administered the compounds in saline s.c. at 5 mg/kg, 10 mg/kg and 20 mg/kg. One group of 20 mice is used as a control group and administered saline s.c. The treatment is repeated at 24, 48, 72 and 96 hours post-challenge.

Compounds of the instant invention show antiviral activity in the above test.

What is claimed is:

1. A compound of the formula

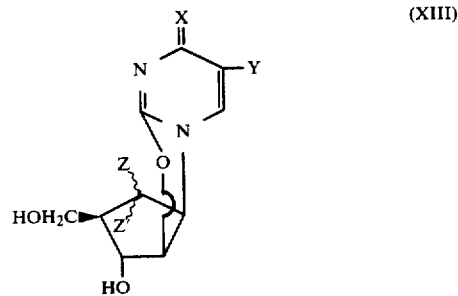

(XIII)

wherein
X is oxygen or NH, Y is hydrogen, iodo, fluoro, methyl or trifluoromethyl;
Z is hydrogen or fluoro and Z' is fluoro; and the wavy line indicates that the group may be above or below the plane of the ring; and the pharmaceutically acceptable acid addition salts thereof.

2. A pharmaceutical composition useful for treating viral infections in mammals which comprises an effective amount of at least one compound of claim 1 or a pharmaceutically acceptable acid addition salt thereof and a pharmaceutically acceptable excipient.

3. A method for treating a mammal for a viral infection which comprises administering an effective amount of at least one compound of claim 1 to a mammal in need thereof.

* * * * *

UNITED STATES PATENT AND TRADEMARK OFFICE
CERTIFICATE OF CORRECTION

PATENT NO. : 4,704,392

DATED : November 3, 1987

INVENTOR(S) : Julien P. H. Verheyden et al

It is certified that error appears in the above-identified patent and that said Letters Patent is hereby corrected as shown below:

In the Abstract, the formula reading

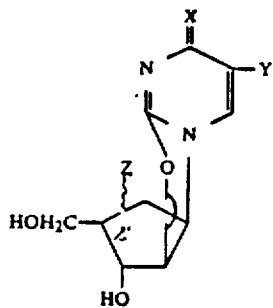   should read   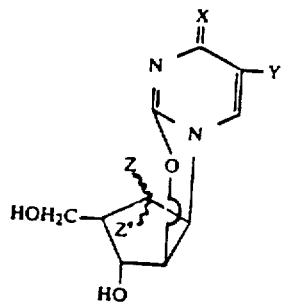

In Column 7, formula IV reading

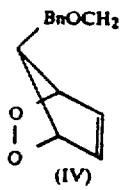   should read   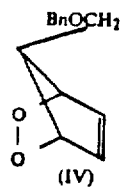

UNITED STATES PATENT AND TRADEMARK OFFICE
CERTIFICATE OF CORRECTION

PATENT NO.  : 4,704,392

DATED       : November 3, 1987                Page 2 of 2

INVENTOR(S) : Julien P. H. Verheyden et al

It is certified that error appears in the above-identified patent and that said Letters Patent is hereby corrected as shown below:

In Column 8, formula V reading

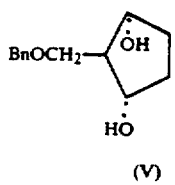  should read  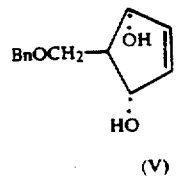

(V)                                (V)

Signed and Sealed this

Twenty-first Day of June, 1988

*Attest:*

DONALD J. QUIGG

*Attesting Officer*          *Commissioner of Patents and Trademarks*